US006458995B1

(12) United States Patent
Cheung et al.

(10) Patent No.: US 6,458,995 B1
(45) Date of Patent: Oct. 1, 2002

(54) CATALYTIC COMPOSITION FOR CARBONYLATION INCLUDING IRIDIUM AND PYRIDINE POLYMERS

(75) Inventors: Hung-Cheun Cheung; Elaine C. Sibrel; G. Paul Torrence, all of Corpus Christi, TX (US)

(73) Assignee: Celanese International Corporation, Dallas, TX (US)

( * ) Notice: Subject to any disclaimer, the term of this patent is extended or adjusted under 35 U.S.C. 154(b) by 0 days.

(21) Appl. No.: 09/540,124

(22) Filed: Mar. 31, 2000

(51) Int. Cl.$^7$ ............................................. C07C 51/12
(52) U.S. Cl. ...................................... 562/519; 562/607
(58) Field of Search .................................. 562/519, 607

(56) References Cited

U.S. PATENT DOCUMENTS

| | | | |
|---|---|---|---|
| 4,127,506 A | 11/1978 | Gray et al. ................. 252/431 |
| 5,155,261 A | 10/1992 | Marston et al. ............. 562/519 |
| 5,281,359 A | 1/1994 | Scates et al. .......... 252/182.16 |
| 5,334,755 A | 8/1994 | Yoneda et al. ............. 562/519 |
| 5,364,963 A | 11/1994 | Minami et al. ............. 562/519 |
| 5,466,874 A | 11/1995 | Scates et al. ............... 562/519 |
| 5,696,284 A | 12/1997 | Baker et al. ............... 560/232 |
| 5,877,347 A | 3/1999 | Ditzel te al. ............... 562/519 |
| 5,877,348 A | 3/1999 | Ditzel et al. ............... 562/519 |
| 5,883,295 A | 3/1999 | Sunley et al. .............. 562/519 |
| 5,892,110 A | 4/1999 | Ramprasad et al. ........ 562/891 |
| 5,932,764 A | 8/1999 | Morris et al. .............. 562/519 |
| 5,942,460 A | 8/1999 | Garland et al. ............. 502/150 |

FOREIGN PATENT DOCUMENTS

| | | | | |
|---|---|---|---|---|
| EP | 0 752 406 A1 | 1/1997 | ........... C07C/51/12 |
| EP | 0 567 331 B1 | 9/1997 | ........... C07C/51/12 |
| EP | 0 849 248 A1 | 6/1998 | ........... C07C/51/12 |
| JP | 5-306253 | 11/1993 | ........... C07C/53/08 |
| JP | 5-306254 | 11/1993 | ........... C07C/53/08 |
| JP | 6-285364 | 10/1994 | ........... B01J/19/00 |
| WO | WO 98/33590 | 8/1998 | ........... B01J/23/46 |
| WO | WO 98/57918 | 12/1998 | ........... C07C/51/12 |

*Primary Examiner*—Paul J. Killos
*Assistant Examiner*—Robert W. Deemie
(74) *Attorney, Agent, or Firm*—M. Susan Spiering

(57) ABSTRACT

An improvement to methanol carbonylation processes utilizing a homogeneous iridium catalyst system comprises adding a rate-promoting amount of an insoluble pyridine ring-containing polymer. Typically, polyvinylpyridine is added to the reactor in amounts of up to about 2 wt. percent.

5 Claims, 1 Drawing Sheet

CATALYTIC COMPOSITION FOR CARBONYLATION INCLUDING IRIDIUM AND PYRIDINE POLYMERS

TECHNICAL FIELD

The present invention relates generally to the manufacture of acetic acid and more particularly to a catalytic composition for use in a methanol carbonylation process including a homogeneous iridium catalyst system and a vinyl-pyridine polymer.

BACKGROUND ART

Polymers are known to be useful in catalytic systems used for carbonylating methanol to make acetic acid. Generally, polymers are suggested in the art as supports for catalysts. There is disclosed in U.S. Pat. No. 5,466,874 to Scates et al. a polymeric carbonylation catalyst system useful for the carbonylation of methanol to make acetic acid, acetic anhydride or both including a polymer support containing pendant pyrrolidone groups which support a rhodium species. See also U.S. Pat. No. 5,281,359 to Scates et al.

U.S. Pat. No. 5,334,755 to Yoneda et al. discloses a process for the production of acetic acid from methanol wherein the liquid system is contacted with a supported rhodium catalyst to produce acetic acid at a temperature from 140–250° C. and a pressure of 15–60 kg/cm$^2$G with a partial pressure of carbon monoxide of 7–30 kg/cm$^2$ while maintaining (a) the water concentration of the solution in the range of 0.5–10% by weight and (b) the carbonylation degree Cη defined therein at 0.15 or more. The supported catalyst is prepared as described in Example 1, columns 9–10, wherein a cross-linked polyvinylpyridine/divinyl benzene copolymer resin is immersed in methanol with various catalysts components and the various components are heated to a relatively high temperature. The catalyst obtained is mixed into a reactant solution including methyl iodide, methanol and acetic acid after the solution is contacted with carbon monoxide in order to make acetic acid.

U.S. Pat. No. 5,364,963 to Minami et al. describes a rhodium catalyst supported on a vinyl pyridine resin useful for making acetic acid. The rhodium is supported on a cross-linked vinyl pyridine resin wherein the vinyl pyridine resin has a cross-link degree of 30–60%, a pore volume of 0.1–0.4 ml/g and an average pore diameter of 20–100 nm. The catalyst may be prepared by contacting the pyridine ring containing resin with an aqueous solution containing rhodium ion and then contacting the resulting rhodium ion carrying resin with carbon monoxide and an alkyl iodide in an organic solvent to convert the rhodium ion to a rhodium complex bound to the resin. Acetic acid is produced by reacting carbon monoxide with methanol at a temperature of 140–250° C. and a partial pressure of carbon monoxide of 7–30kg/cm$^2$ in the presence of an alkyl iodide. See also European Patent Publication No. 0567,331, Japanese Kokai No. 5-306254, Japanese Kokai No. 5-306253, as well as Japanese Kokai No. 6-285364.

U.S. Pat. No. 5,155,261 to Marston et al. discloses an improved Monsanto-type process for acetic acid preparation and a heterogeneous supported catalyst for accomplishing the same. The method comprises reacting methanol with carbon monoxide under a pressure of about 65–80 Bar and temperature of 170–200° C. in the presence of methyl iodide and a catalyst comprising an insoluble polymer having a pendant free base, N-oxide or quaternized pyridine groups supporting a rhodium species loaded to less than 10 weight percent (expressed as metal) of the polymer component.

Iridium has also been utilized as the primary catalytic metal component in homogeneous systems for the catalytic carbonylation of methanol to acetic acid. In European Patent Application Publication No. 0 849 248 there is disclosed a process for the production of acetic acid by carbonylating with carbon monoxide methanol and/or a reactive derivative thereof in a carbonylation reactor containing a liquid reaction composition including an iridium carbonylation catalyst, methyl iodide co-catalyst, a finite concentration of water, acetic acid, methyl acetate and at least one promotor wherein the water concentration is at or below that at which the maximum in the graph of carbonylation rate versus water concentration occurs and there is employed in the liquid reaction composition a co-promotor selected from the alkali metal iodides, alkaline earth metal iodides, metal complexes capable of generating I-, salts capable of generating I- and mixtures of two or more. It is noted on page 4 of the EPA '248 publication that a co-promotor such as lithium should preferably be employed in the range of 0.5 to 1.5:1. That is, the molar ratio of the co-promotor to the iridium is in the range from 0.5:1 to 1.5:1. Polymers have also been reported as useful in these systems.

WIPO Publication WO 98/57918 discloses a process for the production of acetic acid utilizing a vinylpyridine supported Group VIII metal catalyst. In a typical embodiment, about 9 percent by weight of vinylpyridine is charged to a carbonylation reactor. See example 1, p. 10.

Various supports have been specifically suggested for supporting iridium catalyst. There is disclosed in U.S. Pat. No. 5,892,110 to Ramprasad et al. a process for producing acetic anhydride by the reaction of methyl acetate, carbon monoxide and hydrogen at elevated temperatures and pressures in the presence of an alkyl halide and a heterogenous bifunctional catalyst that contains an insoluble polymer having pendant quaternized phosphine groups some of which phosphine groups are ionically bonded to anionic Group VIII metal complexes, the remainder of the phosphine groups being bonded to iodide. The US '110 patent reports than in contrast to earlier processes, no accelerator (promotor) is necessary to achieve the catalytic reaction and the products are easily separated from the catalyst by filtration. The catalyst can be recycled for consecutive runs without loss in activity. In general the catalysts include a polymer, such as a polymer with pendant phosphine groups and a Group VIII metal such as rhodium or iridium. See column 2, lines 55–60.

There is disclosed in WIPO Publication WO 98/33590 a supported catalyst including iridium and at least one second metal selected from the group consisting of ruthenium, molybdenum, tungsten, palladium, platinum and rhenium deposited on a support material. The preferred support materials are carbon, activated carbon, and silicone oxide sources. See page 6, lines 16–18. It should be noted that the WO '590 publication does not disclose polymer supports.

U.S. Pat. No. 4,127,506 to Gray et al. discloses polymer supported catalyst prepared by photo-irradiation of low valent transition metal complexes such as $CO_2(CO)_8$, $Rh_4(CO)_{12}$ or $RU_3(CO)_{12}$ in the presence of solid polymers containing amine ligands such as polyvinylpyridine. Hydroformylation of all olefins to aldehydes at ambient temperatures is specifically disclosed. It should be noted that the US '506 patent reports that the catalysts described therein are useful in a wide variety of reactions including hydrogenation, isomerization, hydroformylation, carbonylation, etc. (See column 3). Among the metals useful in polymer materials there are recited cobalt, nickel, iron, platinum, rhodium, palladium manganese, chromium, titanium, ruthenium, tantalum and iridium. See column 4, lines 15 to 20. The polymer typically contains amine ligands capable of coordinating with the low valent transition metals, preferably tertiary amines such as pyridyl and the like. Among the polymers specifically named are polyvinylpyridine, polyethylene imine, and polyvinylbenzimidazole.

There is disclosed in European Patent Application Publication No. 0 752 406 a process for the production of acetic acid by carbonylation. According to this EPA '406 publication a carbonylation is carried out in the liquid phase in the presence of an iridium carbonylation catalyst, a methyl iodide co-catalyst and a promotor. The beneficial effect of the promotor is enhanced by continuously maintaining the liquid reaction composition no greater than 6.5% by weight water, 1 to 35% by weight methyl acetate and 4 to 20% by weight methyl iodide. It is noted in EPA '406 publication, page 4, lines 28 et seq, and following that, in the iridium system, ionic contaminants such as corrosion metals, phosphines or nitrogen containing compounds or ligands which may quaternize in situ should be kept to a minimum in the reaction composition in order to avoid adverse effects on the reaction by generating $I^-$.

In the foregoing references, the amount of polymer employed is quite high in order to anchor the catalyst metal. It has been found, that contrary to the teachings of the prior art, relatively small amounts of a pyridine polymer is advantageous in a homogeneous, iridium catalyzed system.

SUMMARY OF INVENTION

It has been unexpectedly, and indeed surprisingly, found that the addition of relatively small amounts of a pyridine polymer to a homogeneous iridium catalyst system enhances the carbonylation rate in the manufacture of acetic acid. Relatively small amounts of perhaps as low as 0.01% or even lower and up to about 2 weight percent or perhaps more depending on the system appear to be effective. The homogeneous iridium system is well known and may include various promoters and co-promoters as further described herein. In typical commercial carbonylation processes, methanol and carbon monoxide are utilized as feedstocks.

The present invention thus provides in one aspect for enhanced, iridium-catalyzed carbonylation of methanol and/or its reactive derivatives by way of providing a catalytic composition including: (a) from about 100–6000 ppm iridium; (b) from about 1–70% methyl acetate; (c) from about 1–50% methyl iodide; (d) from about 0.1–15% water and (e) and insoluble pyridine ring containing polymer; wherein the weight ratio of the insoluble pyridine ring containing polymer to iridium is less than about 10.

Typically, the weight ratio of the insoluble ring containing polymer to iridium is less than about 5, with less than about 3 being preferred in some embodiments, whereas the weight ratio of the polymer to iridium is typically at least about 0.1 and preferably at least about 0.5.

Methyl iodide is typically present in the reactor between from about 1 to about 50 weight percent, with from about 2 to about 35 weight percent being more typical. Iridium is preferably present from about 1000 ppm to about 4,000 ppm.

Water should be present in the reaction mixture in at least a finite amount with from about 0.1 to about 15 weight percent being typical and from about 1 to about 10 weight percent being preferred.

Methyl acetate may be present in the catalytic composition in any suitable amount; typically from about 2 to about 50 weight percent, with from about 3 to about 35 weight percent methyl acetate in the reactor being more typical.

A suitable promotor may also be employed if so desired. Typical promoters include osmium compounds and ruthenium compounds as further described herein.

In preferred aspects of the invention, less than about 20 percent of the iridium in the catalytic mixture is anchored on the iridium, wherein from about 0.1 to 1 or up to about 10 percent or less of the iridium being anchored is typically preferred. Thus if a catalytic mixture contains about 4000 ppm iridium, preferably less than about 400 ppm is anchored to the polymer.

Unless otherwise indicated, percent or "%" as used herein refers to weight percent of the reactor mixture and ppm refers to parts per million by weight of the reactor mixture.

BRIEF DESCRIPTION OF DRAWING

The invention is described in detail below with reference to the single FIGURE which includes a plot of space-time-yield ("STY") measured as moles CO/l.hr versus weight percent polyvinylpyridine charged to the reactor as well as a plot (utilizing the same abscissa and an alternate ordinate) of % iridium anchored to the polymer versus weight percent polyvinylpyridine charged to the reactor.

DESCRIPTION OF THE PREFERRED EMBODIMENTS

Figure 1:
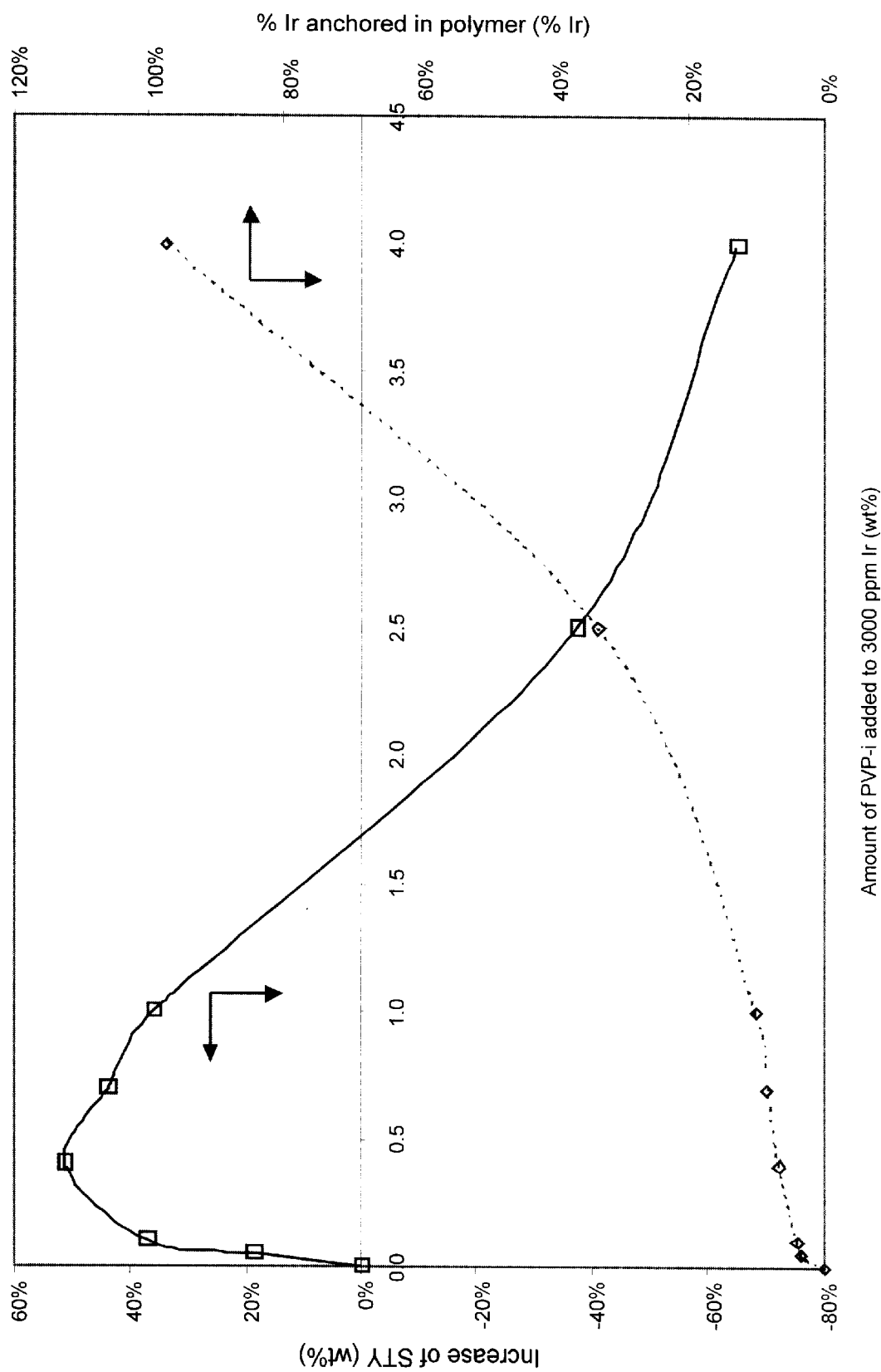

The present invention is directed generally to the carbonylation of methanol and its reactive derivatives with carbon monoxide in a homogeneous catalytic reaction system comprising a reaction solvent (typically acetic acid), methanol and/or its reactive derivatives, a soluble iridium catalyst, at least a finite concentration of water, as well as an insoluble pyridine ring containing polymer and optionally including an osmium or ruthenium promotor. The carbonylation of methanol utilizing iridium catalyst is well known and is generally described in the following U.S. Pat. Nos.: 5,942,460; 5,932,764; 5,883,295; 5,877,348; 5,877,347 and 5,696,284, the disclosures of which are hereby incorporated by reference into this application as if set forth in their entirety. The addition of relatively small amounts of pyridine polymer surprisingly enhances the reaction rates by about 40% or more as further described below.

Suitable reactive derivatives of methanol include methyl acetate, dimethyl ether and methyl iodide. A mixture of methanol and reactive derivatives thereof may be used as reactants in the process of the present invention. Preferably, methanol and/or methyl acetate are used as reactants. At least some of the methanol and/or reactive derivative thereof will be converted to, and hence present as, methyl acetate in the liquid reaction composition by reaction with acetic acid product or solvent. The concentration in the liquid reaction composition of a methyl acetate is suitably in the range of about 1 to 70% by weight, preferably about 2 to 50% by weight, most preferably about 3 to 35% by weight.

Water may be formed in situ in the liquid reaction composition, for example, by the esterification reaction between methanol reactant and acetic acid product. Water may be introduced to the carbonylation reactor together with or separately from other components of the liquid reaction composition. Water may be separated from other components of reaction composition withdrawn from the reactor and may be recycled in controlled amounts to maintain the required concentration of water in the liquid reaction composition. Preferably, the concentration of water in the liquid reaction composition is in the range of about 0.1 to 15% by weight, more preferably about 1 to 15% by weight, most preferably about 1 to 10% by weight.

The iridium catalyst in the liquid carbonylation reaction composition may comprise any iridium-containing compound which is soluble in the liquid reaction composition. The iridium catalyst may be added to the liquid reaction composition for the carbonylation reaction in any suitable form which dissolves in the liquid reaction composition or is convertible to a soluble form. Examples of suitable iridium-containing compounds which may be added to the liquid reaction composition include: $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-H^+$, $[Ir(CO)_2Br_2]^-H^+$, $[Ir(CO)_2I_4]^-H^+$, $[Ir(CH_3)I_3(CO)_2)]^-H^+$, $Ir_4(CO)_{12}$, $IrCl_3.3H_2O$, $IrBr_3.3H_2O$, $Ir_4(CO)_{12}$, iridium metal, $Ir_2O_3$, $Ir(acac)(CO)_2$, $Ir(acac)_3$, (acac) refers to acetyl acetinato, iridium acetate, $[Ir_3O(OAc)_6(H_2O)_3][OAc]$, and hexachloroiridic acid $[H_2IrCl_6]$. More preferably, chloride-free complexes of iridium such as acetates, oxalates and acetoacetates are employed.

The iridium catalyst concentration in the liquid reaction composition is in the range of about 100 to 6000 ppm by weight of iridium, preferably from about 1000 to about 4000 ppm.

Promoters and co-promoters may be used as part of the catalytic system of the present invention as described in European Patent Application Publication No. 0 849 248, the disclosure of which is hereby incorporated by reference. Suitable promoters are selected from ruthenium, osmium, tungsten, rhenium, zinc, cadmium, indium, gallium and mercury, and are more preferably selected from ruthenium and osmium. Ruthenium is the most preferred promoter. Preferably, the promoter is present in an effective amount up to the limit of its solubility in the liquid reaction composition and/or any liquid process streams recycled to the carbonylation reactor from the acetic acid recovery stage. The promoter is suitably present in the liquid reaction composition at a weight ratio of promoter to iridium of about [0.01 to 15]:1, preferably about [0.01 to 10]:1, more preferably about [0.03 to 0.3]:1. A suitable promoter concentration is about 100 to 15,000 ppm.

The promoter may comprise any suitable promoter metal-containing compound which is soluble in the liquid reaction composition. The promoter may be added to the liquid reaction composition for the carbonylation reaction in any suitable form which dissolves in the liquid reaction composition or is convertible to soluble form. Examples of suitable ruthenium-containing compounds which may be used as sources of promoter include ruthenium (III) chloride, ruthenium (III) chloride trihydrate, ruthenium (IV) chloride, ruthenium (III) bromide, ruthenium metal, ruthenium oxides, ruthenium (III) formate, $[Ru(CO)_3I_3]^-H^+$, $[Ru(CO)_2I_2]n$, $[RU(CO)_4I_2]$, $[RU(CO)_3I_2]_2$, tetra(aceto)chlororuthenium(II,III), ruthenium (III) acetate, ruthenium (III) propionate, ruthenium (III) butyrate, ruthenium pentacarbonyl, trirutheniumdodecacarbonyl and mixed ruthenium halocarbonyls such as dichlorotricarbonylruthenium (II) dimer, dibromotricarbonylruthenium (II) dimer, and other organoruthenium complexes such as tetrachlorobis (4-cymene)diruthenium (II), tetrachlorobis(benzene)diruthenium(II), dichloro(cycloocta-1,5 diene) ruthenium (II) polymer and tris(acetylacetonate)ruthenium (III).

Examples of suitable osmium-containing compounds which may be used as sources or promoter include osmium (III) chloride hydrate and anhydrous, osmium metal, osmium tetraoxide, triosmiumdodecacarbonyl, $[Os(CO)_4I_2]$, $[Os(CO)_3I_2]_2$, $[Os(CO)_3I_3]^-H^+$, pentachloro-$\mu$-nitrodiosmium and mixed osmium halocarbonyls such as tricarbonyldichloroosmium (II) dimer and other organoosmium complexes.

Examples of suitable tungsten-containing compounds which may be used as sources of promoter include $W(CO)_6$, $WCl_4$, $WCl_6$, $WBr_6$, $WI_2$, or $C_9H_{12}W(CO)_3$ and any tungsten chloro-, bromo- or iodo-carbonyl compound.

Examples of suitable rhenium-containing compounds which may be used as sources of promoter include $Re_2(CO)_{10}$, $Re(CO)_5Cl$, $Re(CO)_5Br$, $Re(CO)_5I$, $ReCl_3.\chi H_2O$, $[Re(CO)_4I]_2$, $Re(CO)_4I_2]^-H^+$ and $ReCl_5.\gamma H_2O$.

Examples of suitable cadmium-containing compounds which may be used include $Cd(OAc)_2$, $CdI_2$, $CdBr_2$, $CdCl_2$, $Cd(OH)_2$, and cadmium acetylacetonate.

Examples of suitable mercury-containing compounds which may be used as sources of promoter include $Hg(OAc)_2$, $HgI_2$, $HgBr_2$, $HgCl_2$, $Hg_2I_2$ and $Hg_2Cl_2$.

Examples of zinc-containing compounds which may be used as sources of promoter include $Zn(OAc)_2$, $Zn(OH)_2$, $ZnI_2$, $ZnBr_2$, $ZnCl_2$ and zinc acetylacetonate.

Examples of suitable gallium-containing compounds which may be used as sources of promoter include gallium acetylacetonate, gallium acetate, $GaCl_3$, $GaBr_3$, $GaI_3$, $Ga_2Cl_4$ and $Ga(OH)_3$.

Examples of suitable indium-containing compounds which may be used as sources of promoter include indium acetylacetonate, indium acetate, $InCl_3$, $InBr_3$, $InI_3$, $InI$ and $In(OH)_3$.

Preferably, the concentration of methyl iodide in the liquid reaction composition is in the range of about 1 to 50% by weight, preferably about 2 to 30% by weight.

The carbon monoxide reactant may be essentially pure or may contain inert impurities such as carbon dioxide, methane, nitrogen, noble gases, water and $C_1$ to $C_4$ paraffinic hydrocarbons. The presence of hydrogen in the carbon monoxide and generated in situ by the water-gas-shift reaction is preferably kept low, for example, less than about 1 Bar partial pressure, as its presence may result in the formation of hydrogenation products. The partial pressure of carbon monoxide in the reaction is suitably in the range of about 1 to 70 bar, preferably about 1 to 35 bar, and most preferably about 1 to 15 bar.

The pressure of the carbonylation reaction is suitably in the range of about 10 to 200 Bar, preferably about 10 to 100 Bar, most preferably about 15 to 50 Bar. The temperature of the carbonylation reaction is suitably in the range of about 100 to 300° C., preferably in the range of about 150 to 220° C.

Acetic acid is typically used as the solvent for the reaction.

The process of the present invention may be performed as a batch or continuous process, preferably as a continuous process.

The acetic acid product may be removed from the reactor by withdrawing liquid reaction composition and separating the acetic acid product by one or more flash and/or fractional distillation stages from the other components of the liquid reaction composition such as iridium catalyst, ruthenium and/or osmium promotor, methyl iodide, water and unconsumed reactants which may be recycled to the reactor to maintain their concentrations in the liquid reaction composition. The carboxylic acid and/or ester product may also be removed as a vapor from the reactor.

The terminology "pyridine ring-containing polymer", "pyridine polymer" and the like used herein is intended to refer to a polymer containing substituted or non-substituted pyridine rings or substituted or non-substituted, pyridine-containing polycondensed rings such as quinoline rings. The substituents include those inert to the methanol carbonylation such as an alkyl group and alkoxy group. Typical examples of the insoluble, pyridine ring-containing polymers include those obtained by reaction of vinylpyridine with a divinyl monomer or by reaction of vinylpyridine with a divinyl monomer-containing vinyl monomer, such as copolymers of 4-vinylpyridine and divinylbenzene, copolymers of 2-vinylpyridine and divinylbenzene, copolymers of styrene, vinylbenzene and divinylbenzene, copolymers of vinylmethylpyridine and divinylbenzene and copolymers of vinylpyridine, methyl acrylate and ethyl diacrylate. Particularly preferred polymers are described in U.S. Pat. No. 5,334,755 to Yoneda et al., the disclosure of which is incorporated herein by reference. Relatively high degrees of crosslinking in the polymer is most preferred.

It is important that the above pyridine ring-containing polymer should be cross-linked by at least about 10%, preferably at least about 15% or 20% and up to about 75%. A degree of cross-linking below 10% is disadvantageous because the mechanical strength of the polymer may degrade during use. As the degree of cross-linking increases, the availability of the polymer surface may be unduly restricted. A maximum degree of cross-linking of about 50 or 60 percent is then preferred. The term "degree of cross-linking" used herein is intended to refer to the content, in terms of % by weight, of the divinyl monomer, for example.

The pyridine ring of the insoluble polymer may be in the free base or N-oxide form or quaternized form. The insoluble, pyridine ring-containing polymer is preferably in a bead form, more preferably in a spherical form, having a particle diameter of about 0.01–2 mm, preferably about 0.1–1 mm, more preferably about 0.25–0.7 mm. Commercially available pyridine-containing polymers such as Reillex-425® (product of Reilly Tar and Chemical Corporation) and KEX-316®, KeX-501® and KEX-212® (products of Koei Chemical Co., Ltd.) may be suitably used for the purpose of the present invention. As noted above, the amount of polymer employed is generally no more than about 10 times (by weight) of the iridium catalyst in the homogeneous system.

The invention will now be illustrated by way of example. Such examples are not limitative of the invention, the spirit and scope of which is set forth in the appended claims.

EXAMPLES

A series of runs were carried out in a 300 cc Hastalloy B batch autoclave (Autoclave Engineering). Each run lasted about 30 minutes and was conducted at a reactor temperature of about 195° C. and a carbon monoxide pressure of about 400 psig. The procedure for all runs in Table I is described in connection with comparative Example A.

Comparative Example A

The reactants were weighed and charged to the reactor as follows. In the reactor, the solution consisted of water (3.8 g), glacial acetic acid (60.4 g), Iridium (IV) oxide hydrate (3000 ppm, 0.6 g,) (PPG Industries), methyl acetate (33.7 g) (Aldrich) (which equilibrates with methanol and acetic acid), and methyl iodide (20.4 g) (Fisher). The reactor was purged several times with 50 psig of carbon monoxide. After ensuring the reactor was leak-free, the reactor was pressurized to 270 psig and heated to 195° C. Temperature of the reactor was maintained at 195° C., varying by less than 1° C. The temperature was maintained by using an electric heater and adjusted further by cooling water. As the temperature increased, the reactor pressure was raised to 400 psig by adding carbon monoxide from the reservoir. When the reactor solution reached the target conditions, the stirrer was turned on at 800 rpm. Carbon monoxide from the reservoir was introduced to the reactor on pressure demand to maintain 400 psig. This time was recorded as time zero. The carbon monoxide uptake from the reservoir, reactor temperature and reactor pressure were recorded every minute. When carbon monoxide uptake had stopped, the run was completed and the reaction solution was allowed to cool to room temperature.

The rate of gas uptake was measured by plotting the carbon monoxide consumed as a function of time. This rate of gas uptake was then used to calculate the carbonylation rate, as number of moles of reactant consumed per liter of cold degassed reactor composition per hour (mol/l/hr) as space time yield (STY), at a particular reactor composition. The rate was computed as approximately 30 mol/l/hr STY and the results are shown in Table I.

Example 1

The procedure of Comparative Example A was followed, except that about 1% (1.3 g) of 25% crosslinked poly(4-vinylpyridine) ("PVP-I") (Reilly), was added. The carbonylation rate was approximately 43 STY and calculated on the same basis as described in Comparative Example A. After completion of the run, the polymer was digested and analyzed for iridium metal in order to determine the amount of iridium charged which had been anchored to the polymer. Results for this Example appear in Table I.

Examples 2–8

Following the procedure of Example 1, a series of runs were carried out varying the amount of poly(vinylpyridine). Polyvinylpyridine was supplied by either Aldrich or Reilly Industries (Indianapolis. Ind.). Reactor compositions and results appear in Table I.

Comparative Example B

Following substantially the procedure of Comparative Example A, a run was carried out with approximately 2000 ppm iridium and no polyvinylpyridine polymer. Results appear in Table II.

Examples 9–17

Following the procedure of Comparative Example B, a series of runs were carried out with about 2000 ppm iridium catalytic mixture and various amounts of poly(4-vinylpyridine) polymer ("PVP-I") (Aldrich or Reilly). Results appear in Table II.

TABLE I

Effect of polymer, Polyvinylpyridine on 3000 ppm Iridium

|   | [1]PVP-I(wt %) | STY (mole/L-Hr) | Increase of STY (%) | [2]Ir in PVP-I (% Ir) |
|---|---|---|---|---|
| A | 0.0% | 31 | 0% | 0% |
| 1 | 1.00% | 43 | 36% | 10% |
| 2 | 0.05% | 37 | 19% | 3% |
| 3 | 0.10% | 43 | 37% | 4% |
| 4 | 0.40% | 47 | 51% | 7% |
| 5 | 0.50% | 43 | 47% | 8% |

TABLE I-continued

Effect of polymer, Polyvinylpyridine on 3000 ppm Iridium

| [1]PVP-I(wt %) | STY (mole/L-Hr) | Increase of STY (%) | [2]Ir in PVP-I (% Ir) |
|---|---|---|---|
| 6 | 0.70% | 36 | 44% | 8% |
| 7 | 2.5% | 20 | −37% | 33% |
| 8 | 4.00% | 11 | −65% | 97% |

[1]Amount of polyvinylpyridine (PVP-I) in wt % in the reactor. Experiments were run at 195° C.; 400 psia. The reactor materials included approximately 3.0% $H_2O$; 27% MeOAc; 20% MeI and 3000 ppm Ir.
[2]Ir in the polymer is listed in % of Ir. Samples were digested in acid and analyzed for metal. % Ir = {(initial amount of Ir)-(Ir anchored in the polymer)}/(Initial amount of Ir).

TABLE II

Effect of Polymer, Polyvinylpyridine on 2000 ppm Iridium Catalytic System

| | [3]PVP-I (wt %) | STY (mole/l-Hr) | % Increase of STY |
|---|---|---|---|
| B | 0.0% | 23 | 0% |
| 9 | 0.2% | 35 | 48% |
| 10 | 0.4% | 31 | 31% |
| 11 | 0.5% | 25 | 6% |
| 12 | 0.8% | 17 | −3% |
| 13 | 1.0% | 22 | −5% |
| 14 | 1.3% | 16 | −33% |
| 15 | 2.0% | 14 | −41% |
| 16 | 4.0% | 7 | −69% |
| 17 | 7.0% | 0 | −100% |

[3]Amount of polyvinylpyridine (PVP-I) in wt % in the reactor. Experiments were run at 195° C.; 400 psia. The reactor materials included approximately 3.0% $H_2O$; 27% MeOAc; 20% MeI and 2000 ppm Ir.

The data from Table I is presented graphically in FIG. 1, which is a plot of % increase in STY and % Ir anchored in the polymer versus weight percent polyvinylpyridine in the reactor. It can be seen that at low concentrations of polymer, up to about 1.75 percent or so, the reaction rate of the homogeneous iridium catalyst system is enhanced, all other things being equal. The rate enhancement region corresponds to the anchoring of up to about 10 or perhaps 20 percent of the iridium present on the polymer and is greatest at lower degrees of immobilization of the iridium. Runs where from about 1 to about 10 percent of the iridium was anchored exhibited enhanced rates.

The invention has been described in detail and illustrated in connection with several embodiments. Modifications to specific embodiments within the spirit and scope of the present invention will be readily apparent to those of skill in the art. For example, a rhodium co-catalyst could be used with the iridium. Such modifications are within the spirit and scope of the present invention which is set forth in the appended claims.

What is claimed is:

1. In a catalytic system for making acetic acid by way of a carbonylation process including a homogenous iridium catalyst system, the improvement which comprises adding to the reactor composition a rate-promoting amount of an insoluble pyridine ring-containing polymer.

2. The improvement according to claim 1, wherein said insoluble pyridine ring-containing polymer is added in amounts of up to about 2.0 weight percent.

3. The improvement according to claim 2, wherein said insoluble pyridine ring-containing polymer is added in amounts of from about 0.01 to about 2 weight percent of said reactor composition.

4. The improvement according to claim 1, wherein said homogeneous iridium catalyst system includes soluble iridium, methyl acetate, methyl iodide and water.

5. The improvement according to claim 4, wherein said homogeneous iridium catalyst system further includes a promoter or co-promoter selected from the group consisting of ruthenium, osmium, tungsten, rhenium, zinc, cadmium, iridium, gallium, mercury, alkali metal iodides, alkaline earth metal iodides, metal complexes capable of generating $I^-$, salts capable of generating $I^-$ and mixtures thereof.

* * * * *